(12) United States Patent
Candau

(10) Patent No.: US 6,616,918 B2
(45) Date of Patent: Sep. 9, 2003

(54) SELF-TANNING COMPOSITION CONTAINING AN N-ACYL AMINO ACID ESTER AND A SELF-TANNING AGENT

(75) Inventor: Didier Candau, Bièvres (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/197,252

(22) Filed: Jul. 18, 2002

(65) Prior Publication Data

US 2003/0044365 A1 Mar. 6, 2003

(30) Foreign Application Priority Data

Jul. 19, 2001 (FR) .............................. 01 09673

(51) Int. Cl.⁷ .............................. A61K 7/42; A61K 7/44; A61K 7/00
(52) U.S. Cl. .......................... 424/59; 424/60; 424/400; 424/401
(58) Field of Search .................... 424/59, 60, 400, 424/401

(56) References Cited

FOREIGN PATENT DOCUMENTS

| | | |
|---|---|---|
| EP | 0 538 764 | 4/1993 |
| EP | 0 913 390 | 5/1999 |
| EP | 0 968 704 | 1/2000 |
| EP | 1 044 676 | 10/2000 |
| FR | 2 775 595 | 9/1999 |

*Primary Examiner*—Shelley A. Dodson
(74) *Attorney, Agent, or Firm*—Steptoe & Johnson LLP; D. Douglas Price

(57) ABSTRACT

The invention relates to cosmetic and/or dermatological compositions more particularly intended for artificially tanning and/or browning the skin, comprising, in a cosmetically acceptable support, at least one self-tanning agent and at least one N-acyl amino acid ester. The invention also relates to a cosmetic treatment process for artificially tanning and/or browning the skin, comprising applying to the skin an effective amount of the cosmetic and/or dermatological composition. The invention also relates to the use of an N-acyl amino acid ester with the aim of improving the coloration and/or stability of a self-tanning agent in a composition for artificially tanning and/or browning the skin.

22 Claims, No Drawings

SELF-TANNING COMPOSITION CONTAINING AN N-ACYL AMINO ACID ESTER AND A SELF-TANNING AGENT

The present invention relates to a cosmetic and/or dermatological composition more particularly intended for artificially tanning and/or browning the skin and comprising, in a cosmetically acceptable support, at least one N-acyl amino acid ester and at least one self-tanning agent.

The present invention also relates to a cosmetic treatment process for artificially tanning or browning the skin and to the use of an N-acyl amino acid ester for improving the coloration and/or stability of a self-tanning agent.

The invention also relates to the use of these compositions for giving the skin a coloration close to that of natural tanning of the skin.

For the purposes of the present invention, the expression "self-tanning agent" means an agent which, when applied to the skin, especially to the face, gives a tanning effect that is more or less similar in appearance to that which may result from a prolonged exposure to sunlight (natural tan) or a UV lamp.

Nowadays, it is important to have a healthy appearance and tanned skin is always a sign of good health. However, natural tanning is not always desirable since it requires prolonged exposure to UV radiation, in particular to UV-A radiation which causes tanning of the skin, but is also liable to induce reactions or even impairment of the skin, especially in the case of sensitive skin or skin that is continually exposed to solar radiation: erythema, burns, loss of elasticity, appearance of wrinkles, premature ageing. It is thus desirable to find an alternative to natural tanning, which is compatible with the requirements of such skin.

Most of the cosmetic products intended for artificially tanning the skin are based on carbonyl derivatives allowing, by interaction with the amino acids of the skin, the formation of coloured products, among which mention is made of mono- or polycarbonyl compounds such as, for example, isatin, alloxan, ninhydrin, glyceraldehyde, mesotartaric aldehyde, glutaraldehyde, erythrulose and dihydroxyacetone (DHA).

DHA is a particularly advantageous product that is commonly used in cosmetics as an agent for artificially tanning the skin: when applied to the skin, especially to the face, it gives a tanning or browning effect that is similar in appearance to that which may result from a prolonged exposure to sunlight (natural tanning) or a UV lamp.

One drawback of DHA is the slow speed with which the coloration develops: in point of fact, it takes several hours (3 to 5 hours in general) for the coloration to be developed. The intensity of the coloration obtained on the skin and/or its staying power over time (resistance to washing) and/or the speed with which the coloration develops are often considered as insufficient by the users of DHA-based self-tanning compositions.

Another problem posed by DHA-based compositions is that they have the annoying tendency, that is more or less pronounced depending on the nature of the medium in which they are formulated, of degrading over time. These problems associated with the storage and/or conservation of DHA-based compositions are generally reflected in the end by an undesirable yellowing of these compositions.

There is thus increasing demand for fast-acting self-tanning products that give a coloration close to that of natural tanning.

Surprisingly and advantageously, the inventor has found that the use of an N-acyl amino acid ester improves the stability and coloration of compositions comprising a self-tanning agent. The colorations obtained are more chromatic and more stable over time, and also show good water resistance and good homogeneity.

The compositions according to the present invention also have the advantage of having improved cosmetic properties: they give the skin a feeling of softness and freshness, and prevent the skin from drying out and also from having an excessively greasy feel.

The composition according to the present invention comprises, in a cosmetically acceptable support, at least one N-acyl amino acid ester and at least one self-tanning agent.

A subject of the present invention is also the use of the composition according to the invention as a composition for tanning or browning the skin; and a cosmetic process for tanning or browning the skin such that it consists in applying to the skin an effective amount of a composition according to the invention.

Finally, the present invention also relates to the use of at least one N-acyl amino acid ester in compositions for artificially tanning and/or browning the skin, containing at least one self-tanning agent, in order to improve the coloration and/or stability of the self-tanning agent.

The compositions in accordance with the invention give an artificial coloration that is close to that of natural tanning in a short space of time. Thus, an immediate coloration is obtained, which allows visualization of the application and, consequently, better uniformity in the spreading of the composition onto the skin and thus of the resulting coloration. Furthermore, the artificial coloration obtained on the skin according to the invention is extremely close to that of a natural tan.

Other characteristics, aspects and advantages of the invention will become apparent on reading the detailed description that follows.

The N-acyl amino acid ester used in the present invention is an ester of formula:

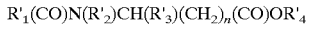

in which:
n is an integer equal to 0, 1 or 2,
$R'_1$ represents a linear or branched $C_5$ to $C_{21}$ alkyl or alkenyl radical,
$R'_2$ represents a hydrogen atom or a $C_1$ to $C_3$ alkyl group,
$R'_3$ represents a radical chosen from the group formed by a hydrogen atom, a methyl group, an ethyl group and a linear or branched $C_3$ or $C_4$ alkyl radical,
$R'_4$ represents a linear or branched $C_1$ to $C_{10}$ alkyl radical or a linear or branched $C_2$ to $C_{10}$ alkenyl radical or a sterol residue.

In the above formula, the group $R'_1(CO)$— is an acyl group of an acid preferably chosen from the group formed by capric acid, lauric acid, myristic acid, palmitic acid, stearic acid, behenic acid, linoleic acid, linolenic acid, oleic acid, isostearic acid, 2-ethylhexanoic acid, coconut oil fatty acids, palm kernel oil fatty acids and hydrogenated palm kernel oil fatty acids. These fatty acids may also contain a hydroxyl group. Even more preferably, the fatty acid is lauric acid.

The portion —$N(R'_2)CH(R'_3)(CH_2)_n(CO)$— of the N-acyl amino acid ester is preferably chosen from the following amino acids: glycine, alanine, valine, leucine, isoleucine, serine, threonine, proline, hydroxyproline, β-alanine, aminobutyric acid, aminocaproic acid, sarcosine or N-methyl-β-alanine.

Even more preferably, the amino acid is sarcosine.

The portion of the N-acyl amino acid esters corresponding to the group OR'$_4$ may be obtained from alcohols chosen from the group formed by methanol, ethanol, propanol, isopropanol, butanol, tert-butanol, isobutanol, 3-methyl-1-butanol, 2-methyl-1-butanol, fusel oil, pentanol, hexanol, cyclohexanol, octanol, 2-ethylhexanol, decanol, lauryl alcohol, myristyl alcohol, cetyl alcohol, cetostearyl alcohol, stearyl alcohol, oleyl alcohol, behenyl alcohol, jojoba alcohol, 2-hexadecyl alcohol, 2-octyldodecyl alcohol and isostearyl alcohol.

These N-acyl amino acid esters may be obtained in particular from natural sources of amino acids. In this case, the amino acids are obtained from the hydrolysis of natural proteins of plants (oat, wheat, soybean, palm or coconut) and then necessarily lead to mixtures of amino acids that will subsequently be esterified and then N-acylated. The preparation of such amino acids is more particularly described in patent application FR 2 796 550, which is incorporated herein by reference.

The amino acid ester that is more particularly preferred for its use in the present invention is isopropyl N-lauroylsarcosinate of formula:

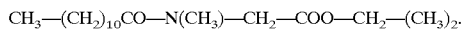

$$CH_3-(CH_2)_{10}CO-N(CH_3)-CH_2-COO-CH_2-(CH_3)_2.$$

These amino acid esters and the process for synthesizing them are described in patent applications EP 1 044 676 and EP 0 928 608 by Ajinomoto Co.

The self-tanning agents are generally chosen from mono- or polycarbonyl compounds such as, for example, isatin, alloxan, ninhydrin, glyceraldehyde, mesotartaric aldehyde, glutaraldehyde, erythrulose, pyrazoline-4,5-dione derivatives as described in patent applications FR 2 466 492 and WO 97/35842, dihydroxyacetone (DHA), and 4,4-dihydroxypyrazoline-5-one derivatives as described in patent application EP 903 342.

The N-acyl amino acid esters are preferably present in the compositions of the invention in concentrations ranging from 0.5% to 50% by weight, and more particularly from 5% to 30% by weight, relative to the total weight of the composition.

In one particularly preferred embodiment of the invention, dihydroxyacetone (DHA) will be used more particularly.

DHA may be used in free form and/or encapsulated, for example in lipid vesicles such as liposomes, described especially in patent application WO 97/25970.

These self-tanning agents may be combined with at least one synthetic or natural direct dye and/or at least one indole derivative, for instance those described in patents EP 425 324 and EP 456 545.

These self-tanning agents may also be combined with other synthetic or natural skin-colouring agents.

For the purposes of the present invention, the expression "skin-colouring agent" will mean any compound with particular affinity for the skin, making it possible to give the skin a long-lasting, non-covering (i.e. not having a tendency to opacify the skin) coloration and which is not removed either with water or using a solvent, and which is resistant both to rubbing and to washing with a solution containing surfactants. Such a long-lasting coloration is thus distinguished from the superficial and transient coloration provided, for example, by a makeup pigment.

The additional colouring agents may also be chosen, for example, from plant extracts such as, for example, "insoluble" extracts of red woods of the genus Pterocarpus and of the genus Baphia, for instance *Pterocarpus santalinus, Pterocarpus osun, Pterocarpus soyauxii, Pterocarpus erinaceus, Pterocarpus indicus* or *Baphia nitida,* for instance those described in patent application EP 971 683.

The colouring agents may also be iron oxide nanopigments, the mean size of the elementary particles of which is less than 100 nm, such as those described in patent application EP 966 953.

The self-tanning agents are generally present in the compositions according to the invention in proportions ranging from 0.1% to 10% by weight relative to the total weight of the composition, and preferably from 0.2 to 8% by weight relative to the total weight of the composition.

The self-tanning compositions in accordance with the invention may be in the form of creams, milks, gels, cream-gels, oil-in-water emulsions, vesicular dispersions, fluid lotions, in particular vaporizable fluid lotions, or any other form generally used in cosmetics, in particular those usually suitable for self-tanning cosmetic compositions.

The compositions in accordance with the present invention may also comprise standard cosmetic adjuvants chosen especially from fatty substances, organic solvents, ionic or nonionic thickeners, softeners, antioxidants, free-radical scavengers, opacifiers, stabilizers, emollients, silicones, α-hydroxy acids, antifoams, moisturizers, vitamins, insect repellants, substance p antagonists, anti-inflammatories, fragrances, preserving agents, surfactants, fillers, polymers other than those of the invention, propellants, acidifying or basifying agents, colorants or any other ingredient usually used in cosmetics and/or dermatology, in particular for the manufacture of self-tanning compositions in the form of emulsions.

The fatty substances may consist of an oil or a wax or mixtures thereof. The term "oil" means a compound that is liquid at room temperature. The term "wax" means a compound that is solid or substantially solid at room temperature, and whose melting point is generally greater than 35° C.

Oils that may be mentioned include mineral oils (paraffin); plant oils (sweet almond oil, macademia oil, blackcurrant pip oil, jojoba oil); synthetic oils, for instance perhydrosqualene, fatty alcohols, fatty acids or fatty esters (for instance the $C_{12}$–$C_{15}$ alkyl benzoate sold under the trade name "Finsolv TN" by the company Finetex, octyl palmitate, isopropyl lanolate, triglycerides, including those of capric/caprylic acids, oxyethylenated or oxypropylenated fatty esters and ethers; silicone oils (cyclomethicone, polydimethylsiloxanes or PDMS) or fluoro oils; polyalkylenes, and mixtures thereof.

Waxy compounds that may be mentioned include paraffin, carnauba wax, beeswax and hydrogenated castor oil.

Among the organic solvents that may be mentioned are lower alcohols and polyols containing not more than 8 carbon atoms.

The thickeners may be chosen especially from crosslinked polyacrylic acids, and modified or unmodified guar gums and celluloses, such as hydroxypropyl guar gum, methylhydroxyethylcellulose and hydroxypropylmethylcellulose.

The compositions in accordance with the invention may also comprise at least one organic photoprotective agent and/or at least one inorganic photoprotective agent that is active in the UVA and/or UVB range (absorbent) and are water-soluble or liposoluble or even insoluble in the cosmetic solvents commonly used.

The organic photoprotective agents are especially chosen from anthranilates; cinnamic derivatives; dibenzoylmethane derivatives; salicylic derivatives; camphor derivatives; triazine derivatives such as those described in U.S. Pat. Nos. 4,367,390, 4,724,137, EP 863 145, EP 517 104, EP 570 838, EP 796 851, EP 775 698, EP 878 469, EP 933 376,EP 506 691, EP 507 692, EP 790 243 and EP 944 624; benzophenone derivatives; β,β-diphenylacrylate derivatives; benzotriazole derivatives; benzalmalonate derivatives; benzimidazole derivatives; imidazolines; bis-benzazolyl derivatives as described in EP 669 323 and U.S. Pat. No. 2,463,264; p-aminobenzoic acid (PABA) derivatives; methylenebis (hydroxyphenyl)benzotriazole derivatives as described in U.S. Pat. Nos. 5,237,071, 5,166,355, GB 2 303 549, DE 197 26 184 and EP 893 119; screening polymers and screening silicones such as those described especially in patent application WO 93/04665; dimers derived from α-alkylstyrene, such as those described in patent application DE 198 55 649, 4,4-diarylbutadienes such as those described in patent applications EP 0 967 200 and DE 197 55 649, and mixtures thereof.

As examples of UV-A-active and/or UV-B-active organic photoprotective agents, mention may be made of the following, denoted hereinbelow under their INCI name:

Para-Aminobenzoic Acid Derivatives
PABA,
Ethyl PABA,
Ethyl dihydroxypropyl PABA,
Ethylhexyl dimethyl PABA sold in particular under the name "Escalol 507" by ISP,
Glyceryl PABA, and
PEG-25 PABA sold under the name "Uvinul P25" by BASF.

Salicylic derivatives:
Homosalate sold under the name "Eusolex HMS" by RonaIEM Industries,
Ethylhexyl salicylate sold under the name "Neo Heliopan OS" by Haarmann and Reimer,
Dipropylene glycol salicylate sold under the name "Dipsal" by Scher, and
TEA salicylate sold under the name "Neo Heliopan TS" by Haarmann and Reimer.

Dibenzoylmethane Derivatives
Butyl methoxydibenzoylmethane sold in particular under the trade name "Parsol 1789" by Hoffmann LaRoche, and
Isopropyldibenzoylmethane.

Cinnamic Derivatives
Ethylhexyl methoxycinnamate sold in particular under the trade name "Parsol MCX" by Hoffmann LaRoche,
Isopropyl methoxycinnamate,
Isoamyl methoxycinnamate sold under the trade name "Neo Heliopan E 1000" by Haarmann and Reimer,
Cinoxate,
DEA methoxycinnamate, and
Glyceryl ethylhexanoate dimethoxycinnamate.

α,α'-Diphenol Acrylate Derivatives
Octocrylene sold in particular under the trade name "Uvinul N539" by BASF, and
Etocrylene sold in particular under the trade name "Uvinal N35" by BASF.

Benzophenone Derivatives
Benzophenone-1 sold under the trade name "Uvinul 400" by BASF,
Benzophenone-2 sold under the trade name "Uvinul D50" by BASF,
Benzophenone-3 or Oxybenzone sold under the trade name "Uvinul M40" by BASF,
Benzophenone-4 sold under the trade name "Uvinul MS40" by BASF,
Benzophenone-5,
Benzophenone-6 sold under the trade name "Helisorb 11" by Norquay,
Benzophenone-8 sold under the trade name "Spectra-Sorb UV-24" by American Cyanamid,
Benzophenone-9 sold under the trade name "Uvinul DS-49" by BASF, and
Benzophenone- 12.

Benzylidenecamphor Derivatives
3-Benzylidenecamphor manufactured under the name "Mexoryl SD" by Chimex,
4-Methylbenzylidenecamphor sold under the name "Eusolex 6300" by Merck,
Benzylidenecamphorsulphonic acid manufactured under the name "Mexoryl SO" by Chimex,
Camphor benzalkonium methosulfate manufactured under the name "Mexoryl SO" by Chimex,
Terephthalylidenedicamphorsulphonic acid manufactured under the name "Mexoryl SX" by Chimex, and
Polyacrylamidomethylbenzylidenecamphor manufactured under the name "Mexoryl SW" by Chimex.

Benzimidazole Derivatives
Phenylbenzimidazolesulphonic acid sold in particular under the trade name "Eusolex 232" by Merck, and
Benzimidazilate sold under the trade name "Neo Heliopan AP" by Haarmann and Reimer.

Triazine Derivatives
Anisotriazine sold under the trade name "Tinosorb 5" by Ciba Specialty Chemicals,
Ethylhexyltriazone sold in particular under the trade name "Uvinul T150" by BASF,
Diethylhexylbutamidotriazone sold under the trade name "Uvasorb HEB" by Sigma 3V, and
2,4,6-Tris(diisobutyl 4'-aminobenzalmalonate) s-triazine.

Benzotriazole Derivatives
Drometrizole trisiloxane sold under the name "Silatrizole" by Rhodia Chimie, and
Methylenebis(benzotriazolyl)tetramethylbutylphenol sold in solid form under the trade name "MIXXIM BB/100" by Fairmount Chemical, or in micronized form as an aqueous dispersion under the trade name "Tinosorb M" by Ciba Specialty Chemicals.

Anthranilic Derivatives
Menthyl anthranilate sold under the trade name "Neo Heliopan MA" by Haarmann and Reimer.

Imidazoline Derivatives
Ethylhexyldimethoxybenzylidenedioxoimidazoline propionate.

Benzalmalonate Derivatives
Polyorganosiloxane containing benzalmalonate functions, sold under the trade name "Parsol SLX" by Hoffmann LaRoche
and mixtures thereof.

The organic photoprotective agents that are more particularly preferred are chosen from the following compounds:
Ethylhexyl salicylate,
Butyl methoxydibenzoylmethane,
Ethylhexyl methoxycinnamate,
Octocrylene,
Phenylbenzimidazolesulphonic acid, Terephthalylidenedicamphorsulphonic acid,
Benzophenone-3,
Benzophenone-4,
Benzophenone-5,
4-Methylbenzylidenecamphor,
Benzimidazilate,
Anisotriazine,
Ethylhexyltriazone,
Diethylhexylbutamidotriazone,
Methylenebis(benzotriazolyl)tetramethylbutylphenol,
Drometrizole trisiloxane,
2,4,6-tris(diisobutyl 4'-aminobenzalmalonate)-s-triazine, and mixtures thereof.

The inorganic photoprotective agents are chosen from pigments or nanopigments (mean size of the primary particles: generally between 5 nm and 100 nm and preferably between 10 nm and 50 nm) of coated or uncoated metal oxides such as, for example, nanopigments of titanium oxide (amorphous or crystallized in rutile and/or anatase form), of iron oxide, of zinc oxide, of zirconium oxide and of cerium oxide, and mixtures thereof. Standard coating agents are, moreover, alumina and/or aluminium stearate. Such coated or uncoated metal oxide nanopigments are described in particular in patent applications EP 518 772 and EP 518 773.

The photoprotective agents are generally present in the compositions according to the invention in proportions ranging from 0.1% to 20% by weight relative to the total weight of the composition, and preferably ranging from 0.2% to 15% by weight relative to the total weight of the composition.

Needless to say, the person skilled in the art will take care to select the abovementioned optional additional compound(s) and/or the amounts thereof such that the advantageous properties intrinsic to the combination in accordance with the invention are not, or not substantially, adversely affected by the envisaged addition(s).

The compositions of the invention may be prepared according to techniques that are well known to those skilled in the art, in particular those intended for preparing emulsions of oil-in-water or water-in-oil type.

This composition may be in particular in the form of a simple or complex emulsion (O/W, W/O, O/W/O or W/O/W emulsion) such as a cream, a milk or in the form of a gel or a cream-gel, in the form of a lotion, a powder or a solid tube, and may optionally be packaged as an aerosol and be in the form of a mousse or a spray.

Preferably, the compositions according to the invention are in the form of an oil-in-water or water-in-oil emulsion.

When it is an emulsion, the aqueous phase of this emulsion may comprise a nonionic vesicular dispersion prepared according to known processes (Bangham, Standish and Watkins, J. Mol. Biol. 13, 238 (1965), FR 2 315 991 and FR 2 416 008).

The invention also relates to a cosmetic treatment process for artificially tanning and/or browning the skin, characterized in that it consists in applying to the skin an effective amount of a cosmetic composition as defined above.

The invention also relates to the use of an N-acyl amino acid ester as defined above with the aim of improving the coloration and/or stability of a self-tanning agent such as those defined above, contained in a cosmetic composition for artificially tanning and/or browning the skin.

Concrete, but in no way limiting, examples illustrating the invention will now be given.

EXAMPLES

Example 1

| O/W EMULSION COMPOSITION | % BY WEIGHT |
|---|---|
| Glyceryl mono/distearate/polyethylene glycol stearate (100 EO) mixture (Arlacel 165 FL - ICI) | 2 |
| Stearyl alcohol (Lanette 18 - Henkel) | 1 |
| Stearic acid from palm oil (Stearine TP - Stearinerie Dubois) | 1.5 |
| Polydimethylsiloxane (Dow Corning 200 fluid - Dow Corning) | 2 |
| α,ω-Dihydroxylated polydimethylsiloxane/cyclopentadimethylsiloxane mixture (14.7/85.3) (Dow Corning 1501 fluid - Dow Corning) | 3 |
| Isopropyl lauroyl sarcosinate (Eldew SL205 - Ajinomoto) | 15 |
| Dihydroxyacetone | 5 |
| Glycerol | 5 |
| Hexadecyl alkyl phosphate, potassium salt (Amphisol K - Hoffmann LaRoche) | 1 |
| Polyacrylic acid (Synthalen K - 3V) | 0.3 |
| Triethanolamine | qs pH:7 |
| DL-α-Tocopheryl acetate (Hoffmann LaRoche) | 0.5 |
| Preserving agents | qs |
| Demineralized water qs | 100 g |

Example 2

| W/O EMULSION COMPOSITION | % BY WEIGHT |
|---|---|
| Oxyethylenated polydimethyl/methylcetyl methylsiloxane (Abil AM 90D - Goldschmidt) | 2 |
| Phenyltrimethylsiloxytrisiloxane (Dow Corning 556 Cosmetic Grade Fluid Dow Corning) | 3 |
| Isopropyl lauroyl sarcosinate (Eldew SL205 - Ajinomoto) | 10 |
| Isohexadecane (Permethyl 101A - Bayer - General Bayer Silicones - Silicones) | 5 |
| Cyclopentadimethylsiloxane (DC 245 Fluid - Dow Corning) | 3 |
| Dihydroxyacetone (Merck) | 3 |
| Glycerol | 5 |
| Magnesium sulphate | 0.7 |
| Perserving agents | qs |
| Demineralized water qs | 100 g |

What is claimed is:

1. A cosmetic and/or dermatological composition, comprising, in a cosmetically acceptable medium:
   (i) at least one self-tanning agent, and
   (ii) at least one N-acyl amino acid ester of formula

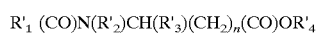

$R'_1(CO)N(R'_2)CH(R'_3)(CH_2)_n(CO)OR'_4$ in which:
   n is a 0, 1 or 2 integer,
   $R'_1$ represents a linear or branched $C_5$ to $C_{21}$ alkyl or alkenyl radical,
   $R'_2$ represents a hydrogen atom or a $C_1$ to $C_3$ alkyl group,
   $R'_3$ represents a hydrogen atom, a methyl group, an ethyl group or a linear or branched $C_3$ or $C_4$ alkyl chain, and R'$_4$ represents a linear or branched C$_1$ to C$_{10}$ alkyl radical, a linear or branched C$_2$ to C$_{10}$ alkenyl radical or a sterol residue.

2. The composition according to claim 1, wherein the amino acid ester is isopropyl N-lauroyl sarcosinate of formula:

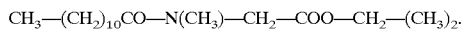

$$CH_3-(CH_2)_{10}CO-N(CH_3)-CH_2-COO-CH_2-(CH_3)_2.$$

3. The composition according to claim 1, wherein the self-tanning agent is a mono- or polycarbonyl compound.

4. The composition according to claim 3, wherein the self-tanning agent is isatin, alloxan, ninhydrin, glyceraldehyde, mesotartaric aldehyde, glutaraldehyde, erythrulose, a pyrazoline-4,5-dione derivative, dihydroxyacetone (DHA) or a 4,4-dihydroxypyrazoline-5-dione derivative.

5. The composition according to claim 4, wherein the self-tanning agent is DHA.

6. The composition according to claim 1, wherein the concentration of the self-tanning agent is from 0.1% to 10% by weight relative to the total weight of the composition.

7. The composition according to claim 1, wherein the composition comprises at least one synthetic or natural direct dye and/or at least one indole derivative.

8. The composition according to claim 1, wherein the composition comprises an additional colouring agent which is an insoluble extracts of a red wood of genus Pterocarpus or of genus Baphia.

9. The composition according to claim 1, wherein the composition comprises an additional colouring agent which is an iron oxide nanopigment, the mean size of the nanopigment being less than 100 nm.

10. The composition according to claim 1, wherein the composition comprises at least one cosmetic adjuvant which is a fatty substance, an organic solvent, an emulsifier, an ionic or nonionic thickener, a softener, an antioxidant, a free-radical scavenger, an opacifier, a stabilizer, an emollient, a silicone, an α-hydroxy acid, an antifoam, a moisturizer, a vitamin, an insect repellent, a substance P antagonist, an anti-inflammatory agent, a fragrance, a preserving agent, a surfactant, a filler, a polymer, a propellant or an acidifying or basifying agent.

11. The composition according to claim 1, wherein the composition also comprises at least one organic photoprotective agent and/or at least one inorganic photoprotective agent that is active in the UVA and/or UVB range.

12. The composition according to claim 11, wherein the organic photoprotective agent is a 1,3,5-triazine derivative, a dibenzoylmethane derivative, a cinnamic derivative, an anthranilate, a salicylic derivative, a camphor derivative, a benzophenone derivative, a β,β-diphenylacrylate derivative, a benzotriazole derivative, a benzalmalonate derivative, a benzimidazole derivative, an imidazoline, a bis-benzazolyl derivative, a p-aminobenzoic acid (PABA) derivative, a methylene bis(hydroxyphenyl)benzotriazole derivative, a screening polymer, a screening silicone, a dimer derived from α-alkylstyrene or a 4,4-diarylbutadiene, or mixtures thereof.

13. The composition according to claim 12, wherein the organic photoprotective agent is:

ethylhexyl salicylate,
butyl methoxydibenzoylmethane,
ethylhexyl methoxycinnamate,
octocrylene,
phenylbenzimidazolesulphonic acid,
terephthalylidenedicamphorsulphonic acid,
benzophenone-3,
benzophenone-4,
benzophenone-5,
4-methylbenzylidenecamphor,
benzimidazilate,
anisotriazine,
ethylhexyltriazone,
diethylhexylbutamidotriazone,
methylenebis(benzotriazolyl)tetramethylbutylphenol,
drometrizole trisiloxane,
2,4,6-tris(diisobutyl 4'-aminobenzalmalonate)-s-triazine,
or mixtures thereof.

14. The composition according to claim 11, wherein the inorganic photoprotective agent is a coated or uncoated metal oxide pigment or nanopigment.

15. The composition according to claim 14, wherein the organic photoprotective agent is a coated or uncoated nanopigment of titanium oxide, iron oxide, zinc oxide, zirconium oxide, cerium oxide, or mixtures thereof.

16. The composition according to claim 11, wherein the photoprotective agent is present in the composition in proportions ranging from 0.1% to 20% by weight relative to the total weight of the composition.

17. The composition according to claim 11, wherein the photoprotective agent is present in the composition in proportion ranging from 0.2% to 15% by weight relative to the total weight of the composition.

18. The composition according to claim 1, wherein the composition comprises from 0.5% to 50% of the N-acyl amino acid by weight relative to the total weight of the composition.

19. The composition according to claim 1, wherein the composition comprises from 5% to 30% of the N-acyl amino acid ester by weight relative to the total weight of the composition.

20. The composition according to claim 1, wherein the composition is in the form of a nonionic vesicular dispersion, an emulsion, a cream or a triple emulsion, a milk, a gel, a cream-gel, a suspension, a dispersion, a mouse or a spray.

21. The composition according to claim 20, wherein the emulsion is an emulsion of water-in-oil type or of oil-in-water type, and the triple emulsion is a W/O/W or O/W/O emulsion.

22. A cosmetic process for tanning or browning skin, composition applying to the skin an effective amount of the cosmetic composition according to claim 1.

* * * * *